US006579722B1

(12) United States Patent
Collins et al.

(10) Patent No.: US 6,579,722 B1
(45) Date of Patent: Jun. 17, 2003

(54) CHEMILUMINESCENCE CHEMICAL DETECTION OF VAPORS AND DEVICE THEREFOR

(75) Inventors: Gregory Earl Collins, Waldorf, MD (US); Susan L. Rose-Pehrsson, Alexandria, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 1239 days.

(21) Appl. No.: 08/500,277

(22) Filed: Jul. 10, 1995

(51) Int. Cl.[7] .............................................. G01N 21/76
(52) U.S. Cl. ........................ 436/172; 436/116; 436/68; 422/83; 422/82.05; 356/39
(58) Field of Search ................................ 436/124, 139, 436/117, 172, 116, 118, 68; 422/83, 88, 82.05, 82.07, 82.8; 356/39

(56) References Cited

U.S. PATENT DOCUMENTS

| 3,774,022 A | 11/1973 | Dubrow et al. |
| 4,713,324 A | 12/1987 | Fox et al. |
| 4,912,032 A | 3/1990 | Hoffman et al. |
| 4,948,975 A | 8/1990 | Erwin et al. |
| 4,965,091 A | 10/1990 | Fratello et al. |
| 5,118,405 A | 6/1992 | Kaneko et al. |
| 5,205,988 A | * 4/1993 | Tanaka et al. ................. 436/52 |
| 5,340,714 A | 8/1994 | Katsilometes |
| 5,582,170 A | * 12/1996 | Soller ...................... 432/82.09 |

OTHER PUBLICATIONS

Rose Pehrsson et al, *Peroxylate, Chemiluminescence Chemical Sensor for $NO_2$*, presented at the 5th International Meeting on Chemical Sensors, Jul. 11, 1994, Rome Italy.

Coulet et al., *Sensors and Actuators B,* 11 (1993) 57–61.
Grate et al., *Anal. Chem.* 1988, 60, 869–875.
Rose–Pehrsson et al., *Anal. Chem.* 1988, 60, 2801–2811.
Hool et al., *Anal. Chem.,* 1988, 60, 834–837.
Freeman et al., *Anal. Chem.,* vol. 50, No. 9, Aug. 1978 (pp 1242–1246).
Paley et al., *Macromolecules,* 1990, 23, 4557–4564.
Schiff et al. *Water Air Soil Pollut.,* 1986, 30, 105–114.
Agranov et al., *Zh. Anal. Khim.,* 1979, 34, 1533–1538 (as translated from).
Mikuška et al., *Anal.Chem.,* 1992, 64, 2187–2191.
McGill et al., *Macromolecules,* 1992, 25, 3015–1019.
McGill et al., *Chemtech,* vol. 24, No. 9, pp. 27–37 (1994).
Hao et al., *Anal. Chem.,* 1994, 66, 3737–3743.
Ray et al., *Anal. Chem.,* 1986, 58, 598–600.
Maeda et al., *Anal. Chem.,* 1980, 52, 307–311.
Wendel et al., *Anal. Chem.,* 1983, 55, 937–940.

* cited by examiner

Primary Examiner—Lyle A. Alexander
(74) Attorney, Agent, or Firm—Joseph T. Grunkemeyer; John J. Karasek

(57) ABSTRACT

A solid phase chemical sensor includes a polymer film which has a chemiluminescent reagent immobilized therein. The polymer film and chemiluminescent reagent are chosen to significantly enhance the selectivity of the sensor to the analyte in the gaseous phase to which the sensor is exposed. The sensor is then positioned so that, when exposed to the gaseous mixture, any chemiluminescence generated will be detected by a photomultiplier tube or other photoelectric device, such as a photodiode. The sensor is particularly useful in the detection of $O_2$, $N_2H_4$, $SO_2$, $NO_2$, and halogenated hydrocarbons.

22 Claims, 7 Drawing Sheets

CHEMILUMINESCENCE CHEMICAL DETECTION OF VAPORS AND DEVICE THEREFOR

BACKGROUND OF THE INVENTION

1. Field of the Invention

The present invention relates generally to chemiluminescence detection and more specifically to the chemiluminescence detection of gaseous analytes.

2. Description of the Background Art

Various chemiluminescence schemes have been successfully applied to the detection of metals, polycyclic aromatic hydrocarbons, and numerous oxidizing and reducing agents. These methods typically rely upon the oxidation of a chemically reactive species, e.g. luminol or lucigenin, by the analyte of interest, and the subsequent emission of a photon from an electronic, excited-state intermediate. Chemiluminescence techniques are free of Raman and Rayleigh scattering, interferences associated with fluorescence techniques, and, therefore, permit the operation of a photomultiplier tube at maximum sensitivity. The primary attraction of chemiluminescence detection is the excellent sensitivity obtainable over a wide dynamic range using simple instrumentation.

The vast majority of work done in the chemiluminescence field has been devoted to solution-based, flow injection analysis formats. One of the most widely investigated chemiluminescence reagents is 3-aminophthalhydrazide, or luminol. Luminol has been effectively used for the detection of many different metals and oxidants in solution, due to the catalytic behavior these metals have on the chemiluminescent oxidation of luminol. Examples include the detection of Cr(III), Co(II), Fe(II), $H_2O_2$(aq), NO(aq), and ClO-(aq). These methods require adequate mixing of the reagent and unknown solutions prior to passage before a photomultiplier tube (PMT), accurate control of the solution delivery to the PMT, and the consumption of a substantial amount of reagents.

Different instrumental variations, based upon the chemiluminescent oxidation of luminol, have been devised for the detection of gas-phase oxidants. Maeda et al., *Anal. Chem.*, 1980, 52, 307–311, designed a chemiluminescent reaction compartment for the detection of $NO_2$(g) which collected a pool of alkaline, luminol solution directly below a PMT, and introduced the sampled air stream into the region above the solution. Excess luminol solution and air flowed continuously out of the reaction compartment through an outlet port at the base of the system. This system was very sensitive to movements of the compartment, and had a relatively slow time response.

An alternate design for the chemiluminescent detection of $NO_2$(g) was subsequently presented by Wendel et al., *Anal. Chem.*, 1983, 55, 937–940, wherein a length of filter paper was positioned adjacent to a PMT, and a flow of alkaline, luminol solution was directed down the paper in a fine film. This system has also been used for the measurement of trace levels of ambient ozone, utilizing the chemiluminescent dye, eosin Y. *Anal. Chem.*, 1986, 58, 598–600. A further variation on the instrument described by Wendel et al. led to the development of a commercially available instrument devoted to the measurement of $NO_2$(g), the Luminox® LMA-3 (Scintrex/Unisearch); a detailed description of this instrument was presented by Schiff et al. *Water Air Soil Pollut.*, 1986, 30, 105–114. The reaction cell consists of a fabric wick positioned in front of a PMT that is continually wetted with fresh luminol solution delivered via a peristaltic pump, and whose surface is exposed to a stream of the ambient air pumped through the cell. In recent years, this instrument has been utilized in combination with various pretreatment stages for the trace detection of organic nitrates. Blanchard et al., *Anal. Chem.*, 1993, 65, 2472–2477; Hao et al., *Anal. Chem.*, 1994, 66, 3737–3743. Still another variation on the luminol chemiluminescent detector for $NO_2$(g) was introduced by Mikuška et al., *Anal. Chem.*, 1992, 64, 2187–2191; this configuration employs a continuous spray of luminol solution, directed immediately below the PMT, and generated from a stream of the analyzed gas.

Each of the systems referenced above requires accurate and continual pumping or delivery (e.g. peristaltic pump) of an aqueous luminol solution, be it across a piece of filter paper, a wick, or mixed with an additional solution and/or gas containing the analyte of interest. The systems described above are not amenable to remote sensing or personal dosimeter applications because of constraints with respect to size, weight, power, or portability.

The industrial community is continually striving to develop sensor systems which are simpler, less expensive, more compact, and offer the possibility for remote sensing or personal dosimeter applications. In order to address some of these constraints, efforts have been made to develop a solid-phase, chemiluminescent, chemical sensor.

Previous authors have demonstrated the feasibility of utilizing luminol in a reagent-less fashion, i.e. using a solid substrate support. Agranov and Reiman attempted the direct application of luminol, sodium carbonate, and copper sulfate onto indicator tape for the detection of hydrogen peroxide, but were plagued by humidity and stability problems. Agranov et al., *Zh. Anal. Khim.*, 1979, 34, 1533–1538. Freeman and Seitz determined hydrogen peroxide concentrations in solution by immobilizing luminol and peroxidase within a polyacrylamide gel held on the end of a fiber optic probe. Freeman et al., *Anal. Chem.*, 1978, 50, 1242–1246. The co-immobilization of dehydrogenase enzymes and luminol within a polyvinyl alcohol matrix has been proposed for the detection of ATP or NAD(P)H. Coulet, et al., *Sensors and Actuators* B, 1993, 11, 57–61. Luminol has also been covalently immobilized onto silica particles for the detection of hydrogen peroxide by flow injection analysis. Hool et al., *Anal. Chem.*, 1988, 60, 834–837.

Generally, the analytical use of chemiluminescence requires selectivity for the analyte. In most, but not all, chemiluminescent systems, this need for selectivity presents problems.

SUMMARY OF THE INVENTION

Accordingly, it is an object of this invention to detect a gaseous material with a solid-phase chemiluminescent sensor.

It is another object of the present invention to provide a small, portable chemiluminescent sensor for the detection of gaseous analytes.

It is a further object of the present invention to vary the sensitivity of a solid-phase chemiluminescent sensor to favor the detection of a selected gaseous analyte in a mixture of gaseous materials.

These and additional objects of the invention are accomplished by a solid phase chemical sensor including a polymeric film which has immobilized therein a chemiluminescent reagent, a catalyst, if desired, and a buffer, if desired. The polymeric film and chemiluminescent reagent are chosen to significantly enhance the selectivity of the sensor to the analyte in the gaseous phase to which the sensor is exposed. Similarly, any catalyst or buffer used are also selected to significantly enhance the selectivity of the sensor to the analyte in the gaseous phase to which the sensor is exposed. The sensor is then positioned so that, when exposed to the gaseous mixture, any chemiluminescence generated will be detected by a photomultiplier tube or other photoelectric device, such as a photodiode.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements, wherein.

DESCRIPTION OF THE PREFERRED EMBODIMENTS

Figure 1A:
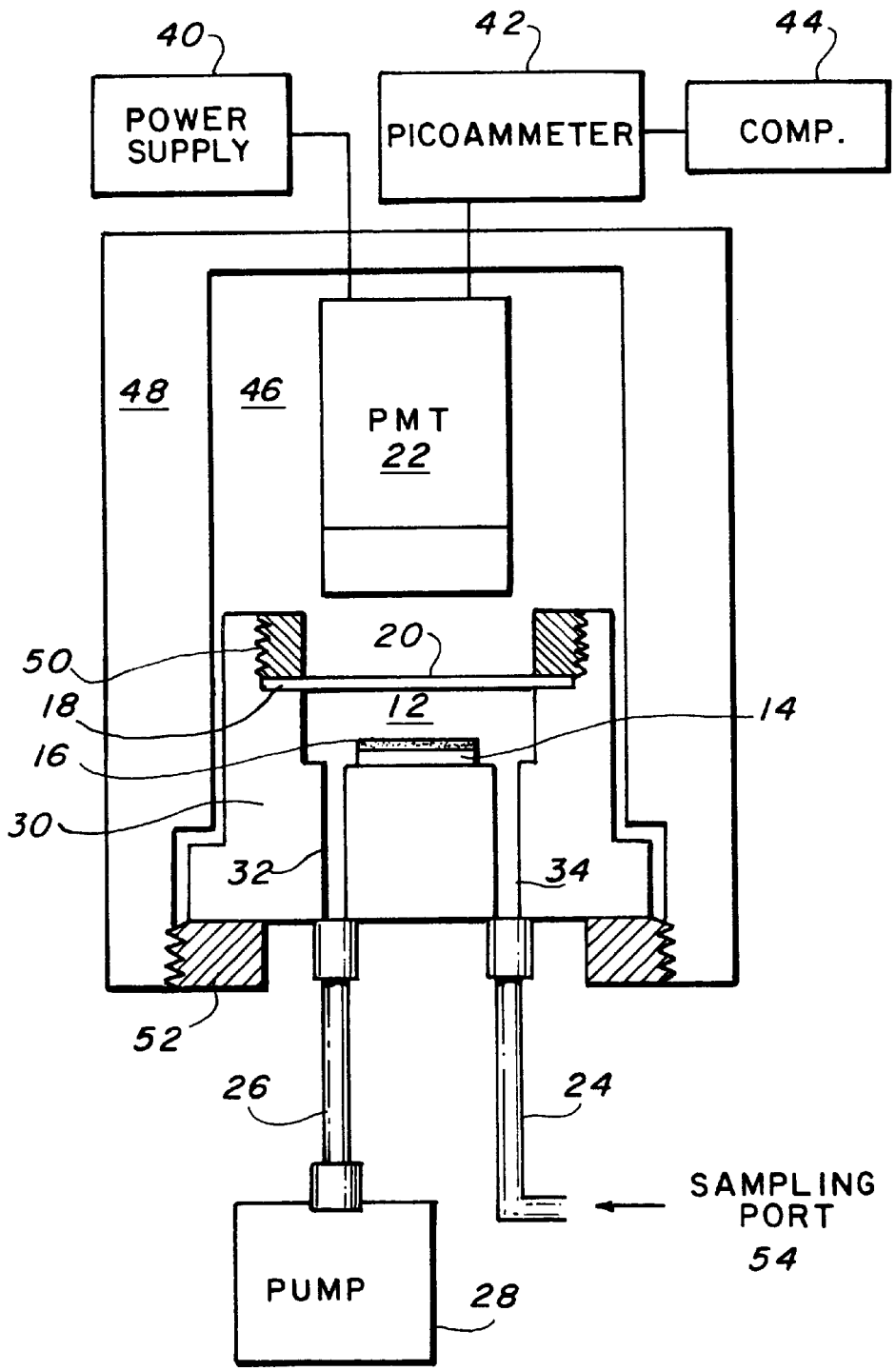
FIG. 1a shows an apparatus for practicing the present invention.

A significant feature of the present invention is the selection of a polymeric film that preferentially or selectively sorbs or concentrates the analyte. In the present specification and claims, the terms "preferential" or "selective" sorption will be used interchangeably with the terms "preferential" or "selective" concentration, and will have the same meaning. As a result of this selective concentration, the amount of analyte that can react with the chemiluminescent reagent to provide a detectable signal is significantly increased over the amount that would be present in the absence of the polymeric film.

With regard to the general method taught and claimed herein, the specific polymeric film used is not critical. With regard to any selected analyte (either a single compound or a class of compounds), however, the selection of an appropriate polymeric film is critical. The relative sorption of an analyte by a particular matrix may be determined empirically or, in some cases, predicted theoretically by calculations.

The sorbent properties of various polymers have been characterized with respect to their hydrogen bond acidity and basicity, dipolarity, polarizability, and ability to distinguish between members of a homologous series. Rose-Pehrsson, et al., *Anal. Chem.*, 1988, 60, 2801–2811, the entirety of which is incorporated herein by reference for all purposes. Grate et al., *Anal. Clem.* 1988, 60, 869–875, the entirety of which is incorporated herein by reference for all purposes, discusses the partitioning of a solute vapor between the gas phase and a stationary polymeric film. As shown in that paper, the relative retention times of various vapor phase analytes on a gas-liquid chromatography (GLC) column reliably indicates the relative sorption of the analytes by a film of composition similar to that of the GLC column. The solubility interactions of polymeric film and solute vapor can, in some cases, be quantitatively determined by the use of solvatochromic parameters. These solvatochromic parameters describe the dipolar and hydrogen bonding properties of the solute vapors and the polymeric film. Methodologies for predicting partition coefficients for any vapor with any characterized phase use the equation:

$$\log K = \text{constant} + s\pi^* + a\alpha + b\beta + l \log L^{16}$$

which appears in Abraham et al., *Polymer* 1987, 28, 1363–1369, the entirety of which is incorporated herein by reference for all purposes.

In the above equation, the parameters $\pi^*$, $\alpha$, $\beta$, and $\log L^{16}$ characterize the solute vapor. $\pi^*$ measures the ability of a compound to stabilize a neighboring charge or dipole. For nonprotonic, aliphatic solutes with a single dominant dipole, $\pi^*$ values are approximately proportional to the molecular dipole moments. $\alpha$ and $\beta$ measure solute hydrogen bond acidity and hydrogen bond basicity, respectively. $L^{16}$ is the Ostwald solubility coefficient (partition coefficient) of the solute vapor in hexadecane at 25° C. and provides a measure for dispersion interactions. The coefficients s, a, b, and l, are determined by multiple regression analysis and characterize the stationary phase. For example, b, as the coefficient for solute hydrogen bond basicity, provides a measure of the stationary phase hydrogen bond acidity. For any particular stationary phase/vapor interaction, evaluation of the individual terms (such as $b\beta$) and comparison of their magnitudes allow the relative strengths of various solubility interactions to be sorted out and examined.

Of primary interest in the method of the present invention is the detection of $O_2$, $N_2H_4$, $SO_2$, $NO_2$, and halogenated hydrocarbons (for example, $CHCl_3$, $CCl_4$, and $CH_2Cl_2$). For the detection of halogenated hydrocarbons, a heated platinum or similar catalytic filament may be placed in the gas inlet lines leading from the sampling port to the sensing cell containing the polymeric film. The polymeric films useful in the method of the present invention are typically, but not necessarily, hydrogels or solvatochromic polymers. Typical polymeric films useful in the method of the present invention include fluorbpolyol (FPOL), poly(ethylene maleate) (PEM), poly(epichlorhydrin) (PECH), poly(vinylpyrrolidone) (PVP), ethyl cellulose (ECEL), poly(butadiene) hydroxylated (PBOH), poly(ethyleneimine)

(PEI), poly(ethylene phthalate) (PEPH), poly(isoprene/fluoro alcohol) (PFA), poly(isobutylene) (PIB), FOMBLIN Z-DOL® (a perfluoropolyether diol made by Aldrich); polyacrylamide (PAC), poly(ethylene oxide) (PEO), polyvinyl alcohol, and superabsorbent polymers such as WaterLock polymer D-242®. Typically, a superabsorbent polymer can absorb at least 200 times its weight in water. Most superabsorbent polymers absorb 500 or more times their weight in water.

Any chemiluminescent reagent responsive to the analyte may be used in the method of the present invention. Typical chemiluminescent reagents include, but are not limited to 3-aminophthalhydrazide (luminol) dimethylbisacridinium nitrate (lucigenin), siloxene or 2,4,5-triphenylimidazole (lophine). Peroxyoxalate chemiluminescent reagents, for example bis(2,4,6-trichlorophenyl)oxalate (TCPO) and perylene, may be applied to the sensitive determination of strong oxidizers, such as hydrogen peroxide, as well as fluorescers, including polyaromatic hydrocarbons. By selecting a chemiluminescent reagent that is significantly more responsive to the analyte of interest than to the other components of the gaseous mixture, the specificity of the present invention may be further enhanced.

Various chemiluminescence pathways may be used in the method of the present invention. For example, an electroactive chemiluminescent reagent, such as tris(2,2'-bipyridyl) ruthenium(III) ($Ru(bpy)_3^{3+}$), can be continually regenerated following the emission of a photon, to give the active form of the molecule. By simply applying a potential to a gel, solution, or wetted membrane of $Ru(bpy)_3^{2+}$ to oxidize the molecule from $Ru(bpy)_3^{2+}$ to $Ru(bpy)_3^{3+}$, the chemiluminescent reagent can be continually regenerated. The use of $Ru(bpy)_3^{3+}$ as a chemiluminescent reagent for the detection of vapors is further discussed in Collins et al., "Chemiluminescent Chemical Sensors for Inorganic and Organic Vapors," *Proceedings of the 8th Intemadonal Conference on Solid State Sensors and Actuators: Eurosetisors* IX, Royal Swedish Academy of Engineering Sciences, IVA, Stockholm, Sweden, 1995, pp 768–771 (extended abstract); Collins et al., "Chemiluminescent Chemical Sensors for Inorganic and Organic Vapors," submitted to *Sensors and Actuator*, B in June 1995 (full paper), the entirety of each of which are incorporated by reference herein for all purposes. The technology for using $Ru(bpy)_3^{3+}$ in solution for the detection of gases and vapors may be readily extended to the use of $Ru(bpy)_3^{3+}$ immobilized on or in selectively sorbent polymers for the detection of gases and vapors. $Ru(bpy)_3^{3+}$ is particularly useful in the chemiluminescence detection of hydrazines such as $HCH_3N_2H_2$, or $(CH_3)_2N_2H_2$.

A catalyst may be used to further enhance the specificity of the present invention for the selected analyte. To accomplish this end, the catalyst should significantly boost the chemiluminescent responsiveness of the chemical reagent to the analyte over any chemiluminescence emissions resulting from the presence of other components in the gaseous mixture being tested. Typically, catalysts useful in the present invention are inorganic, and are most often metals or metal ions from inorganic metal salts. Catalysts useful in the present invention include, but are not limited to $Fe_2(SO_4)_3$, $CuCl_2$, $MnSO_4$, $CoCl_2$, $K_3Fe(CN)_6$, $NaSO_3$, and colloidal platinum.

The chemiluminescent reagent and catalyst within the film should be effective to provide for a detectable response to the presence of a predetermined threshold concentration of analyte in the gaseous mixture. Many chemiluminescent reactions are well-known. Thus, a person of ordinary skill in the art, guided by the present specification, can readily determine the desired concentrations of chemiluminescent reagent and catalyst for a wide variety of analytes and threshold concentrations, without undue experimentation.

Where the polymeric film is a hydrogel, care should be taken to prevent water loss from the film. This goal can be accomplished by, for example, sandwiching the gel between a viewing window and a semipermeable membrane that allows the diffusion of analytes from a stream of the gaseous mixture while limiting the loss of water. One example of such a membrane is a Teflon® (a perfluorinated polymer) film.

The specificity of the present invention may also be improved by appropriately adjusting the pH within the polymeric sensing film. Typically, pH is adjusted by incorporating a buffer into the polymeric sensing film. The appropriate buffer and the buffered pH will depend upon the chemiluminescent reaction, the analyte, and the components of the mixture that might potentially interfere with accurate detection and/or quantification of the analyte.

FIG. 1*a* shows a typical setup for practicing the present invention. As shown in FIG. 1*a*, small flow-through cell 12 has within it a glass substrate 14. Glass substrate 14 supports a polymeric sensing film 16. Glass plate 18 covers cell 12 and forms window 20 in full view of PMT 22. PMT 22 rests within chamber 46 formed by the interior of housing 48. Inlet and outlet tubes (made, for example, of Teflon®) 24 and 26, respectively, allow vacuum pump 28 (MSA Flow-Lite Turbo) to sample air directly across the surface of sensing film 16 and are wrapped with black heat shrink tape to prevent the entry of light. Flow-through cell 12 is a cavity defined by the interior of plug 30 and by glass plate 18. Threaded ring 50 screws onto the threaded upper end of plug 30 and holds glass plate 18 tightly against the top of flow-through cell 12. Gas passages 32 and 34 extend from inlet and outlet tubes 26 and 24, respectively, through plug 30 and into flow through cell 12. Threaded ring 52 screws onto the threaded lower end of housing 48 and holds plug 30 tightly in place against housing 48 to seal chamber 46 and flow-through cell 12 from light. Air from sampling port 54 enters inlet tube 24, flows into inlet passage 34, flows across sensing film 16 and into outlet passage 32. From outlet passage 32, the sampled air flows through outlet tube 26 and is then expelled by vacuum pump 28. Power supply 40 powers PMT 22. Picoammeter 42 monitors the cathodic current from PMT 22. The data collected from picoammeter 42 is sent to computer 44, where it is collected by an appropriated data acquisition program such as National Instruments' LABView® for Windows®.

Figure 1B:
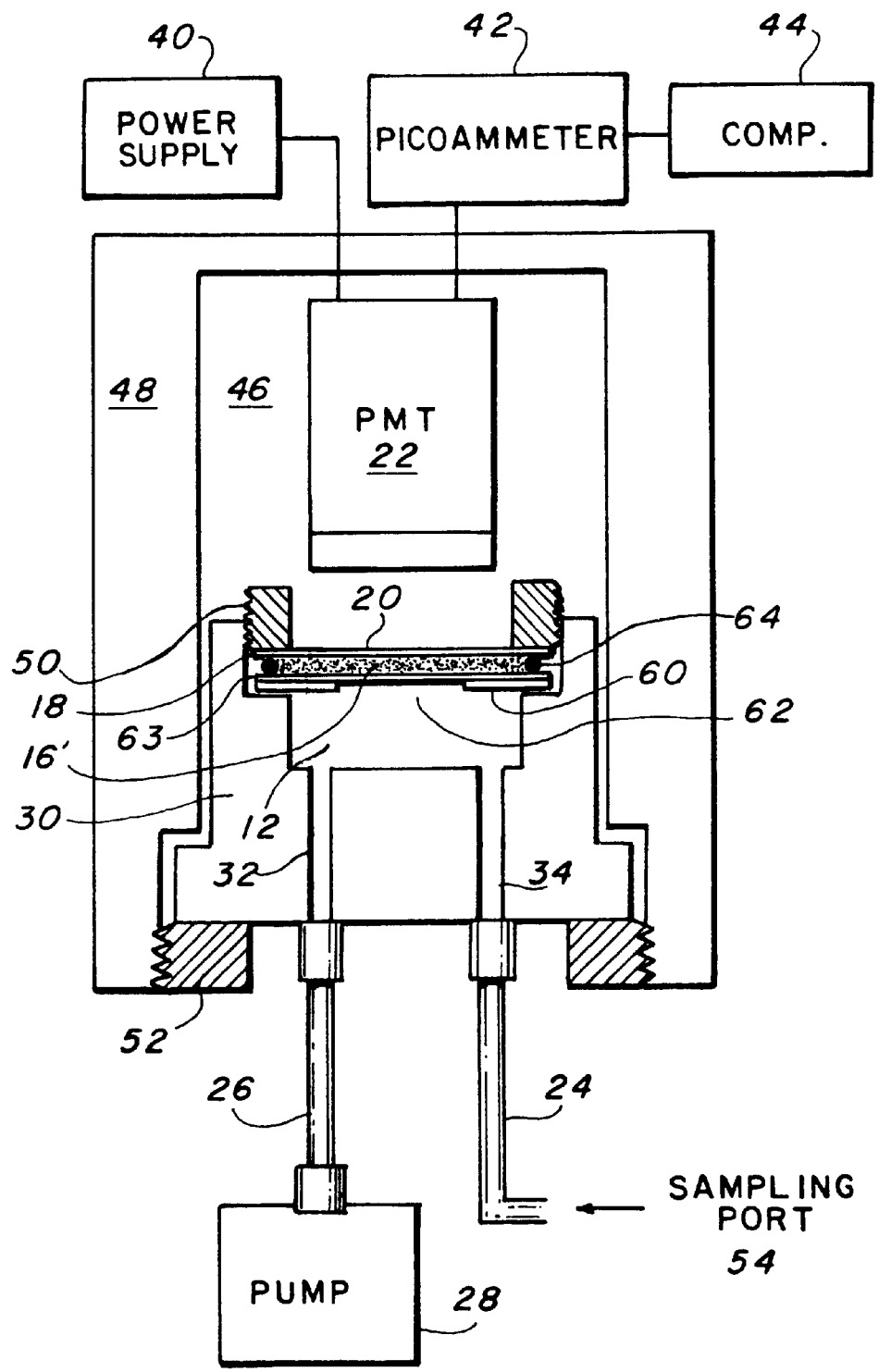
FIG. 1b shows an alternative apparatus for practicing the present invention.

FIG. 1*b* shows an alternative arrangement for use when the polymeric film of the sensing film is a hydrogel. Except where noted below, the components of the device of FIG. 1*b* are identical to their like-numbered counterparts in the device of FIG. 1*a*. In the device of FIG. 1*b*, hydrogel sensing film 16' is supported on a teflon support 60. Opening 62 is defined by teflon support 60. The bottom surface of hydrogel sensing film 16' rests on a thin teflon membrane 63. The purpose of teflon membrane 63 is to permit the diffusion of analytes from the air stream into hydrogel sensing film 16', while preventing the loss of water from the hydrogel. Hydrogel sensing film 16' and teflon membrane 63 are sandwiched between teflon support 60 and glass plate 18, within a space defined by o-ring 64. In the arrangement of FIG. 1*b*, the sampled gas flows across the bottom surface of teflon membrane 63. The sampled gas diffuses through teflon membrane 63 into hydrogel sensing film 16'.

The thickness of the polymeric film can be empirically adjusted to compromise between greater lifetime (thicker films) and faster response times (thinner films). In each of the following examples, the sprayed polymeric films used were several microns thick, and the hydrogels were several millimeters thick.

Figure 2:
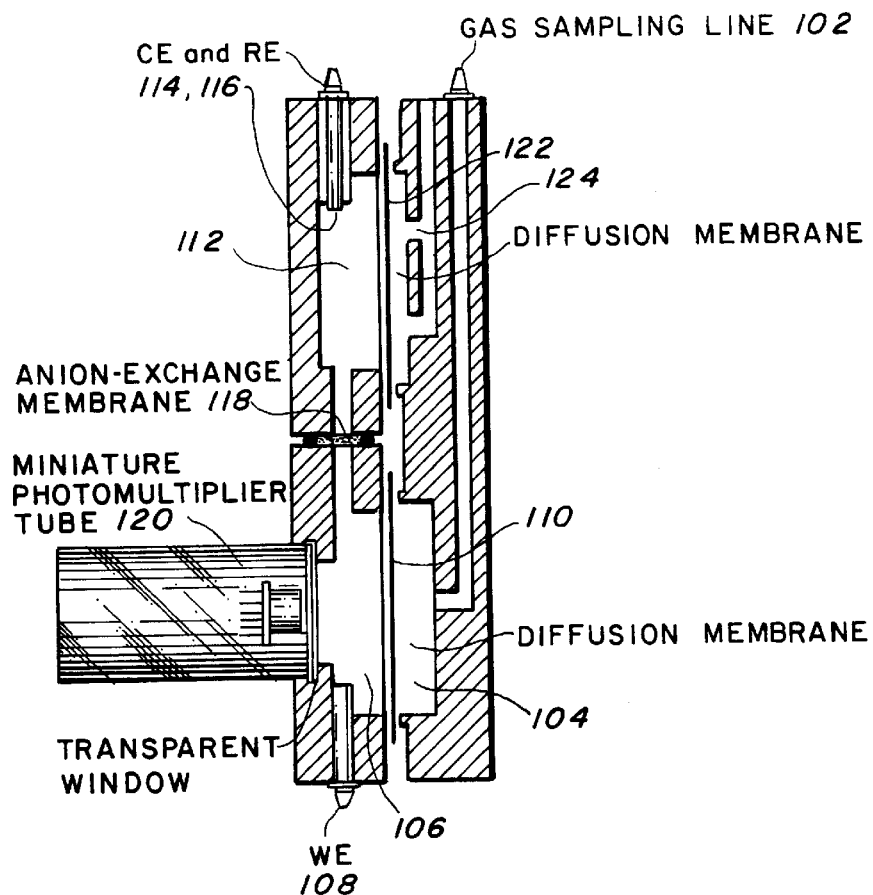
FIG. 2 shows an apparatus for practicing chemiluminescence detection of gas vapors using $Ru(bpy)_3^{3+}$ in solution.

FIG. 2 shows an apparatus for practicing chemiluminescence dectection of gas vapors using $Ru(bpy)_3^{3+}$ in solution. Gas sampling line 102 (or other sampling means such as a port or a diffusion membrane) samples the gaseous mixture suspected of containing the analyte vapor. Sample chamber 104 is in communication with gas sampling line 102 (or other sampling means such as a port or a diffussion membrane). Reaction chamber 106 contains a solution, gel, or wetted membrane of $Ru(bpy)_3^{2+}$ and houses working electrode 108 for oxidizing the $Ru(bpy)_3^{2+}$ in the reaction chamber to $Ru(bpy)_3^{3+}$. Reaction chamber 106 is isolated from sample chamber 104 by a semipermeable membrane 110 (of, for example, Teflon®). Semipermeable membrane 110 allowing any analyte in the sample chamber to diffuse into the solution in reaction chamber 106. If desired, semipermeable membrane 110 may be selected to allow selective diffusion of the analyte vapor.

Reference chamber 112 houses counter electrode 114 and reference electrode 116 (hidden behind counter electrode 114 in FIG. 2). Reference chamber 112 is in fluid communication with the reaction chamber 106, but is typically also isolated from reaction chamber 106 by anion exchange membrane 118. Photomultiplier tube 120 is positioned to detect the chemiluminescent reduction of $Ru(bpy)_3^{3+}$ to $Ru(bpy)_3^{2+}$ in reaction chamber 106. If desired, a photodiode or other light detector may be used in place of photomultiplier tube 120. The detection of chemiluminescence in reaction chamber 106 indicates the presence of the analyte vapor of interest in the sample gas.

To allow the escape of byproduct gases from reference chamber 112, a second semipermeable membrane 122 is positioned between reference chamber 112 and vent passages 124. Semipermeable membrane 122 allows gases to diffuse from reference chamber 112 to vent passages 124. Vent passages 124 vent the diffused gases to the outside. While the chemical sensor of FIG. 2 uses a solution of $Ru(bpy)_3^{3+}$, the chemiluminescent reagent $Ru(bpy)_3^{3+}$ may also be immobilized on a selective membrane such as Nafion®.

Having described the invention, the following examples are given to illustrate specific applications of the invention including the best mode now known to perform the invention. These specific examples are not intended to limit the scope of the invention described in this application.

EXAMPLES

Apparatus

For runs where the sensing film was a hydrogel, the apparatus of FIG. 1b was used, with a PTFE membrane (0.47 cm or size) (Gelman Sciences) for protecting the hydrogel. For other runs, the apparatus of FIG. 1a was used. In each case, the vacuum pump was a MSA Flow Lite Turbo® and the air was sampled directly across the surface of the sensing film at a rate of 2 L/min. Also, in each case, a Keithley 485® picoammeter was used to monitor the cathodic current, and National Instruments LABView for Windowso controlled the data acquisition.

Chemicals and Gas Mixtures

All chemicals were used as received from the suppliers. The following is a list of the polymeric sorbent coatings and hydrogels examined, the abbreviation used, and the corresponding manufacturer name: polyethyleneimine (PEI, Phase Separations); fluoropolyol (FPOL, synthesized in-house (O'Rear et al., *J. Paint Technol.*, 1971, 43, 113–119) with the structure $[OCH_2CH(OH)CH_2OC(CF_3)_2(C_6H_4)C(CF_3)_2OCH_2CH(OH)CH_2OR-]_n$, where n=5–10 and R=—$CH_2(CF_2)_3CH_2$— for FPOL1, R=—$(CF_3)_2$CCHCHCH— for FPOL2, and R=—$(CH_2)_4$— for FPOL3); FOMBLIN Z-DOL, perfluoropolyether diol (Aldrich); polyacrylamide (PAC, synthesized from N,N'-methylenebis (acrylamide) and acrylamide (Aldrich) according to a previously published procedure); 4% polyvinyl alcohol (PVAL, Aldrich, 99% hydrolyzed) crosslinked with sodium borate; poly(ethylene oxide) (PEO, Union Carbide Corp.); Super-Absorbing Polymer (SAP, Absorbent Technology Co.); WaterLock SuperAbsorbent polymer D-242 (Grain Processing Corp.). The 3-Aminophthalhydrazide (luminol) (97%) was purchased from Aldrich and used to prepare a 0.01 M stock solution in 0.1 M KOH. The metal salts used for the catalytic studies included: $Fe_2(SO_4)_3$, $CuCl2$, $MnSO_4$, $CoCl_2$, $K_3Fe(CN)_6$, $Na_2SO_3$, colloidal platinum prepared by reducing hydrogen hexachloroplatinate(IV) with ascorbic acid (Collins, et al., *Talanta*, 42 (1995) 543–551), and colloidal platinum prepared by reducing $PtCl_4$ with sodium citrate (Matheson, et al., *J. Phys. Chem.*, 1983, 87, 394–399).

Gas mixtures (86 ppm $NO_2$ in air, 103 ppm $O_2$ in He, 110 ppm NO in air, 99.8 ppm $SO_2$ in air, and 450 ppm $NH_3$ in nitrogen) were obtained from either Scott Specialty Gases or Matheson, and diluted by air using Matheson 8200® mass flow controllers to give varying concentration levels. The hydrazine vapor generation system has been described elsewhere, and was used to generate hydrazine levels from 10–500 ppb in air. Grate, et al., *Langmuir*, 1988, 4, 1293–1301. Humidity was controlled through the use of bubblers and line mixers, and quantitated using a Hygrodynamics® hygrometer.

Film Preparation

The polymeric, thin films were prepared by exhaustively spraying a basic, methanolic solution of the polymer, luminol and metal catalyst onto a glass substrate (8 cm$^2$) using an air brush (Badger Model 200-3). In general, the hydrogels were prepared by adding 1 ml of $10^{-4}$ M luminol (pH 13 in KOH) to 0.02 g of the resin.

Results

Because the sensitivity of these sensors is directly linked to the background chemiluminescence, it was critical that all light leaks through the sampling ports be eliminated. Providing that the inlet and outlet tubes are long enough (>30 in) and sufficiently masked with black, heat-shrink tubing, the background chemiluminescence in the absence of any analytes (i.e. in an atmosphere of ultrahigh purity nitrogen) could be reduced to the room temperature baseline response of the photomultiplier tube (0.5 nA).

Figure 3:
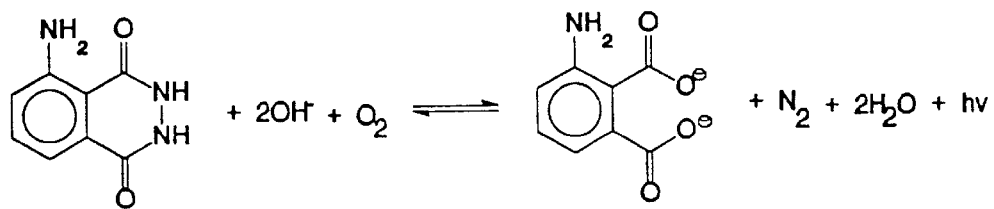
FIG. 3 shows the chemiluminescence reaction arising from the oxidation of luminol by $O_2(g)$

The oxidation of 3-aminophthalhydrazide, luminol, by oxygen results in the emission of a photon of light (~440 nm) according to the chemical reaction shown in FIG. 3. This reaction occurs under basic conditions, and is catalyzed by numerous metal and metal cation species. The luminol-immobilized, polymeric thin films were initially characterized with respect to oxygen exposure in order to determine those substrate conditions necessary for suppressing any chemiluminescence arising from $O_2(g)$ interactions with the film. The sensitivity of these chemiluminescent, chemical sensors for $NO_2(g)$ was dramatically improved by lowering the background chemiluminescence evident from the oxidation of luminol by the high concentration of $O_2(g)$ in air. In addition, by suppressing the reaction of luminol with oxygen, the lifetime of these sensors is improved by maintaining the luminol and metal catalyst concentration within the polymeric film.

The polymeric, luminol-immobilized, chemiluminescent films were prepared as described above, using an air brush to exhaustively spray the contents of a methanolic solution containing the chemiluminescent reagents and polymer onto a small, quartz slide (8 $cm^2$). Initial studies focused on the effect of KOH on the responsiveness of luminol-immobilized ($6.2 \times 10^{-8}$ moles/$cm^2$) polyethyleneimine ($6.2 \times 10^{-3}$ g/$cm^2$) films incorporating Co(II) as the metal catalyst ($1.2 \times 10^{-8}$ moles/$cm^2$). Shown in Table 1 are the sensitivities (amps/ppm $O_2(g)$ in $N_2(g)$) observed with respect to the detection of oxygen for several different polymeric films, each of which was prepared identically, with the exception of the quantity of KOH deposited onto the glass slide during spraying. It is evident from this table that the optimum concentration of KOH for the detection of oxygen is approximately $2 \times 10^{-4}$ moles/$cm^2$, with the sensitivity dropping off significantly on either side of this concentration level within the polymeric film. As will be discussed in more detail later, films prepared for the detection of nitrogen dioxide utilize a much lower concentration of KOH (e.g. $2 \times 10^{-5}$ moles/$cm^2$) within the film, in order to adequately suppress the chemiluminescence background signal arising from the direct oxidation of luminol by oxygen.

TABLE 1

Sensitivities obtained for the detection of oxygen in nitrogen utilizing a polyethyleneimine film incorporating Co(II) and varying levels of KOH onto a glass slide (8 $cm^2$)

| [KOH] on Glass Slide (moles/$cm^2$) | Sensitivity to $O_2(g)$ ((amps/ppm) × $10^{-12}$) |
|---|---|
| 0 | 0.00 |
| 2.23 × $10^{-5}$ | 0.00 |
| 1.15 × $10^{-4}$ | 0.308 |
| 2.06 × $10^{-4}$ | 0.593 |
| 2.97 × $10^{-4}$ | 0.586 |
| 4.49 × $10^{-4}$ | 0.200 |

The particular metal catalyst chosen for immobilization within the polymeric film had a significant influence upon the sensitivity that the film exhibited for oxygen. Table 2 summarizes the sensitivities obtained for a series of polyethyleneimine films grown onto quartz slides, each incorporating identical concentrations of catalyst ($1.2 \times 10^{-8}$ moles/$cm^2$), KOH ($2 \times 10^{-4}$ moles/$cm^2$), polymer ($6.2 \times 10^{-3}$ g/$cm^2$) and luminol ($6.2 \times 10^{-8}$ moles/$cm^2$). Notably, the sensitivity for $O_2(g)$ obtained from a film containing $Fe(CN)_6^{3-}$ was nearly unmeasurable, while the sensitivity seen using $Fe_2(SO_4)_3$ was nearly $8 \times 10^{-13}$ amps/ppm $O_2(g)$ in nitrogen. Ferricyanide is certainly a catalyst to consider for situations requiring a low oxygen background, while $Fe_2(SO_4)_3$ appears to be the catalyst of choice for the detection of $O_2(g)$.

A number of different polymer coatings were investigated and compared for the detection of oxygen (see Table 2). Each of the films were prepared with identical concentrations of polymer ($2.5 \times 10^{-3}$ g/$cm^2$), KOH ($2 \times 10^{-4}$ moles/$cm^2$), metal catalyst (Fe(III), $1.2 \times 10^{-8}$ moles/$cm^2$) and luminol ($6.2 \times 10^{-8}$ moles/$cm^2$), with the exception of the control case, in which no polymer was used. In each case, the presence of a polymeric, sorbent coating on the glass slide for the immobilization of the chemiluminescent reagents resulted in an enhancement of the sensitivity. The sensor utilizing FPOL3 was found to be nearly 10 times more sensitive to oxygen. This effect is attributable to the increased chemical sorption of oxygen by the polymer on the glass slide.

TABLE 2

Chemiluminescence sensitivities obtained for the detection of oxygen while using various metal catalysts immobilized within a polyethyleneimine thin film. Effect of the polymer sorbent coating on the chemiluminescence sensitivity obtained for the detection of oxygen (Fe(III) used as the metal catalyst).

| | Polymer Type (Sensitivity given in (amps/ppm) × $10^{-12}$) | | | | | |
|---|---|---|---|---|---|---|
| Metals | PEI | FPOL 2 | Fomblin | FPOL 1 | FPOL 3 | None |
| $Fe_2(SO_4)_3$ | 0.797 | 1.11 | 1.13 | 2.22 | 2.61 | 0.448 |
| Co(II) | 0.593 | | | | | |
| Mn(II) | 0.518 | | | | | |
| Cu(II) | 0.323 | | | | | |
| Pt(ascorbic) | 0.280 | | | | | |
| $K_3Fe(CN)_6$ | 0.00 | | | | | |

Figure 4:
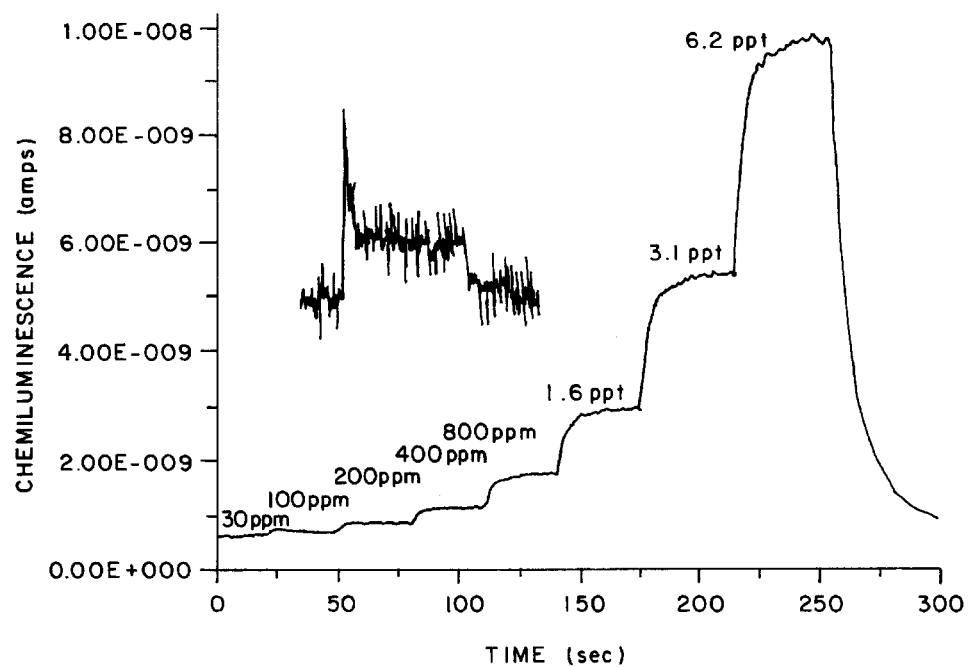
FIG. 4 is a graph showing the effects of introducing varying levels of oxygen in a nitrogen carrier stream to a thin film of fluoropolyol immobilizing luminol, Fe(III) and KOH. The inset is an example of the signal/noise seen for the detection of 2.4 ppm oxygen in nitrogen.

From the optimization studies, a chemiluminescent chemical sensor was prepared for the sensitive determination of trace levels of oxygen via the incorporation of luminol ($6.2 \times 10^{-8}$ moles/$cm^2$), KOH ($2 \times 10^{-4}$ moles/$cm^2$) and $Fe_2(SO_4)_3$ ($1.2 \times 10^{-8}$ moles/$cm^2$) within a thin film of FPOL3 ($2.5 \times 10^{-3}$ g/$cm^2$). FIG. 4 illustrates the chemiluminescent response of this sensor to increasing levels of oxygen in nitrogen. A detection limit of 2.4 ppm $O_2$ in nitrogen (signal/noise=2:1; see insert of FIG. 4) was obtained with a response time of several seconds (r>0.99). In a similar fashion to the films prepared for the detection of $NO_2(g)$ which will be discussed in the following section, the sensitivity was observed to slowly decrease (1%/hour) with exposure to 20 ppm $O_2(g)$. We attribute this gradual change in the film's response to the continual and irreversible change in luminol concentration occurring at the surface of the polymeric thin film. Thus, the usable lifetime of these films was strongly dependent upon the concentration and extent of exposure to oxygen. For this reason, this embodiment of a sensor according to the present invention is best suited to the trace detection of oxygen within an inert atmosphere, e.g. monitoring low levels of oxygen during the fabrication of micro-semiconductor devices. In general, for continuous monitoring of low ppm quantities of oxygen, the polymeric films should be replaced on a daily basis in order to maintain an accuracy of 10%.

Figure 5:
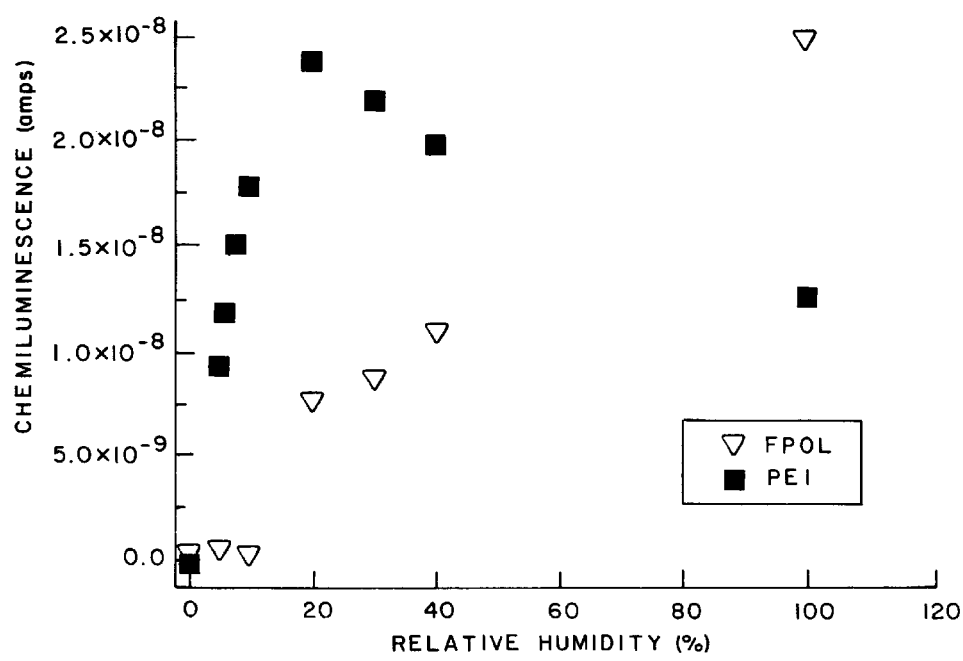
FIG. 5 is a graph showing the effect of humidity on the chemiluminescence response of polyethyleneimine and fluoropolyol thin films (immobilizing luminol and colloidal platinum) to 1.0 ppm $NO_2$.

Initial attempts at preparing a chemical sensor for $NO_2(g)$ relied upon the same polymeric, sorbent coatings and conditions investigated for oxygen, with the exception that a much lower concentration of KOH ($2 \times 10^{-5}$ moles/$cm^2$) was employed in order to significantly lower the background chemiluminescence evident from the oxidation of luminol by $O_2(g)$. These polymeric films exhibited a strong humidity dependence for the detection of $NO_2(g)$. FIG. 5 is a plot of the plateau chemiluminescence response observed for the introduction of 1 ppm $NO_2(g)$ in air to two different films, FPOL2 and PEI, while varying the relative humidity of the air stream from 0–100%. Both of these films immobilized identical concentrations of colloidal platinum ($1.2 \times 10^{-8}$ moles/$cm^2$) and luminol ($6.2 \times 10^{-8}$ moles/$cm^2$). Under dry conditions, no chemiluminescence response was seen for either film to the introduction of $NO_2(g)$. As the humidity level was increased, the two polymeric matrices exhibited dynamically different behavior. For the FPOL2 film, the chemiluminescence response increased steadily with increasing relative humidity. The PEI film, on the other hand, showed a maximum in chemiluminescence at approximately 20% relative humidity, which decreased with increasing humidity. Notably, the peak chemiluminescence intensities observed were identical for both films, albeit at two different relative humidities.

These results can be better understood by examining the solubility characteristics of these polymers with respect to the adsorption of water, a property which has been previously quantitated using surface acoustic wave devices. Polyethyleneimine is a polymer with hydrogen bond accepting functionalities that interact specifically with water. Fluoropolyol, on the other hand, is considered to be a hydrogen bond acid due to the fluorinated carbon atoms found along its polymer backbone, and, as a result, adsorbs several times less water vapor. From FIG. 5, it is evident that water absorption into these two different polymers plays a critical role in the chemiluminescent reaction scheme involving $NO_2(g)$. Apparently, the solvating properties of water permit the formation of free $OH^-$ ions from KOH crystallites contained within the polymeric film. This effect was most clearly seen for the FPOL film, which exhibited a nearly linear increase in its chemiluminescence response to 1 ppm $NO_2(g)$ with the increase in relative humidity. The PEI film, on the other hand, strongly adsorbed water vapor into the film even at much lower relative humidities, and for this reason, exhibited a peak in the chemiluminescence at a much lower level (20% versus nearly 100%). As the relative humidity exceeds 20%, the overall chemiluminescence signal to 1 ppm $NO_2(g)$ decreased due to the competition the film expressed for the chemisorption of water vapor, as opposed to $NO_2(g)$.

In order to eliminate the effect of humidity on sensitivity, the chemiluminescent reagents were immobilized within polymeric hydrogels sandwiched between a quartz glass window and a Teflon®, PTFE membrane (FIG. 1b). The membrane served two purposes: 1) preventing the rapid evaporation of water from the hydrogel; and 2) permitting the diffusion of analytes across the membrane into the hydrogel. The immobilization of luminol and a metal catalyst within a hydrogel provided a suitable matrix for supporting the chemiluminescent reaction in either dry or wet air with identical sensitivity.

Table 3 shows a compilation of the sensitivities ((amps/ppm)$\times 10^{-9}$) observed in the quantitation of $NO_2(g)$ and a number of other gases of analytical interest, for a series of hydrogels immobilizing the chemiluminescent reagents. Although film-to-film reproducibility was not extensively investigated, initial studies have indicated that for a given set of three films prepared under identical conditions, the film-to-film reproducibility is within 6–8%. Reproducibility could be improved through careful control of the film thickness and placement within the sensor compartment cell. A detailed description of each hydrogel and the immobilization procedure utilized is given in the experimental section. Also listed for comparison are the sensitivities of two polymeric coatings, PEI and FPOL2 at their optimum relative humidity. Note first, that the detection of $NO_2(g)$ using PEI and FPOL2 was inferior to the sensitivities observed for the majority of hydrogels examined. Just as was seen for the case of oxygen, the detection of $NO_2(g)$ was strongly dependent upon the polymeric composition of the hydrogel used to support the chemiluminescent reagents. Of the different hydrogels examined, the water soluble resin Waterlock provided the highest sensitivity with respect to the detection of $NO_2(g)$. Previously, Wendel et al. demonstrated that the addition of $Na_2SO_3$ to a solution of luminol and metal catalyst will result in a significant enhancement of the chemiluminescence signal seen for the detection of nitrogen dioxide. Wendel, et al., *Anal. Chem.*, 1983, 55, 937–940. The present results support this observation for luminol-immobilized hydrogels, wherein the addition of sodium sulfite to an otherwise identical Waterlock hydrogel more than doubled its sensitivity to $NO_2(g)$.

TABLE 3

Compilation of the sensitivities (amps/ppm) $\times 10^{-9}$) observed for the detection of $NO_2(g)$ and other possible interferents while using various hydrogels for immobilizing luminol, KOH and colloidal platinum (citrate reduced).

| | Sensitivity ((amps/ppm) $\times 10^{-9}$) | | | | |
|---|---|---|---|---|---|
| Polymer | $NO_2(g)$ | $N_2H_4(g)$ | $SO_2(g)$ | $NO(g)$ | $NH_3(g)$ |
| SAP | 76.5 | 0.7 | 0.03 | 0.00 | 0.00 |
| PEO | 52.6 | 0.6 | 0.0 | 0.00 | 0.00 |
| PAC | 4.6 | 0.00 | 0.00 | 0.00 | 0.00 |
| Waterlock | 186 | 0.3 | 0.3 | 0.00 | 0.00 |
| Waterlock* | 389 | 4.5 | 0.03 | 0.00 | 0.00 |
| PVAL | 48.5 | 0.2 | 0.05 | 0.00 | 0.00 |
| PVAL* | 806 | no data | 0.03 | no data | 0.00 |
| PEI(20% RH) | 11.2 | 0.06 | 0.00 | 0.00 | 0.00 |
| FPOL(88% RH) | 21.2 | 0.00 | 0.00 | 0.00 | 0.0 |

*0.01M $Na_2SO_3$.

In Table 4, a series of sensitivities are tabulated for the hydrogel, polyvinyl alcohol, immobilizing luminol ($5\times 10^{-4}$ M/L) and a series of different metal catalysts ($10^{-4}$ M/L), all prepared under identical conditions. While $Fe_2(SO_4)_3$ seemingly provided the best sensitivity to $NO_2(g)$, the chemiluminescence response obtained using this metal catalyst was unstable, with the plateau response slowly decreasing with time. For this reason, the use of the metal catalysts, colloidal platinum (citrate reduced) and Cu(II) is preferred for the quantitation of $NO_2(g)$.

TABLE 4

Sensitivities ((amps/ppm) $\times 10^{-9}$) observed for the detection of $NO_2(g)$ and other possible interferents while using a series of transition metal catalysts immobilized within a pH 13, polyvinyl alcohol film.

| | Sensitivity ((amps/ppm) $\times 10^{-9}$) | | | | |
|---|---|---|---|---|---|
| Metals | $NO_2(g)$ | $N_2H_4(g)$ | $SO_2(g)$ | $NO(g)$ | $NH_3(g)$ |
| $Fe_2(SO_4)_3$ | 110 | 2.2 | 0.08 | 0.00 | 0.00 |
| $K_3Fe(CN)_6$ | 76.3 | 1.6 | 0.06 | 0.00 | 0.00 |
| Cu(II) | 95.0 | 66.2 | 0.01 | 0.00 | 0.00 |
| Pt(citrate) | 48.5 | 0.2 | 0.05 | 0.00 | 0.00 |
| Pt(ascorbic) | 44.2 | 2.0 | 0.01 | 0.00 | 0.00 |
| Co(II) | 42.9 | 20.9 | 0.6 | 0.00 | 0.00 |

Figure 6:
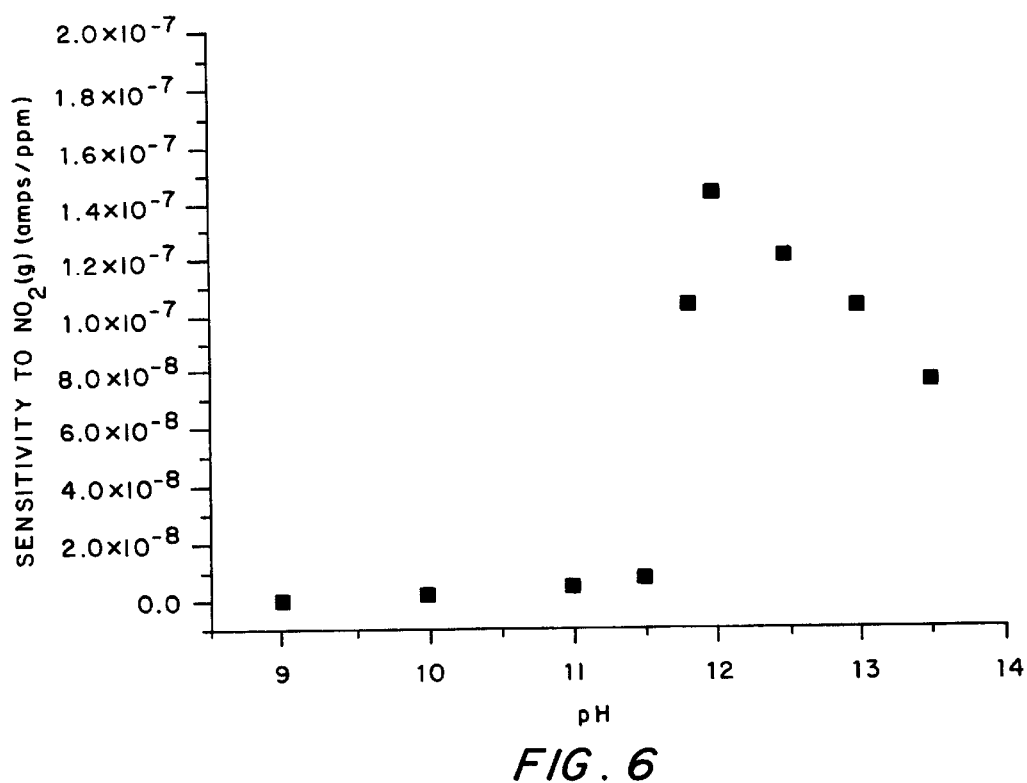
FIG. 6 is a graph showing the influence of the pH of a Waterlock hydrogel on the sensitivity obtained for the detection of $NO_2(g)$ (Cu(II) used as the metal catalyst).

Just as was seen in the case of oxygen detection, $NO_2(g)$ determinations using these chemiluminescent chemical sensors were strongly dependent upon the relative pH of the hydrogel. For the chemiluminescent detection of oxygen, extremely alkaline conditions were necessary on the surface of the polymeric film. The optimal pH for the detection of $NO_2(g)$, on the other hand, occurred in a pH region where the background chemiluminescence from oxygen is minimal. FIG. 6 is a plot of the change in sensitivity with pH for a Waterlock® polymer incorporating luminol and Cu(II) in the detection of $NO_2(g)$. The most striking observation to be made from this figure is the sharp onset of chemiluminescence intensity above pH 11.5. The importance of this result is that some selectivity was tailored into these devices by simply adjusting the relative pH of the hydrogel being utilized. For example, the present invention is useful for the chemiluminescence detection of chlorinated (as well as other halogenated) hydrocarbons, by using a pre-oxidation step with a heated Pt filament. This chemistry is operable at pH 11 with little loss in sensitivity for the chlorinated hydrocarbons, but with a dramatic (>30 times) reduction in the interference effect of $NO_2(g)$. Any catalytic metal filament, such as Ir, may be used in place of Pt.

Figure 7:
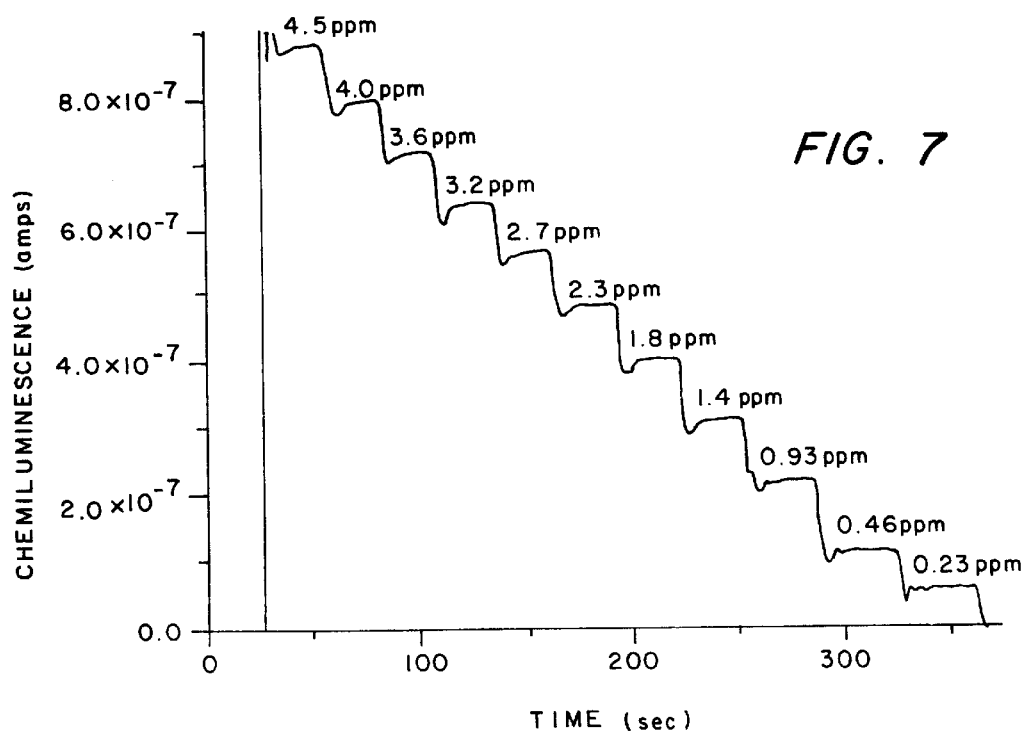
FIG. 7 is a graph showing the response of a polyvinyl alcohol film immobilizing luminol and colloidal platinum (citrate reduced) to the introduction of varying levels of $NO_2(g)$ in a carrier stream of dry air.

The sensitive detection of part-per-trillion levels of nitrogen dioxide in air was demonstrated in a Waterlock hydrogel incorporating luminol and the metal catalyst, colloidal Pt (citrate reduced)(see FIG. 7). The downward spikes evident in FIG. 7 are artifacts associated with the solenoid valve within the gas flow controller adjusting to the lower flow requirement for the analyte gas. Response times were on the order of seconds, with a detection limit as low as 460 ppt (signal/noise ratio=3:1) and error bars for point to point reproducibility of ±2%. While the linearity of response was excellent (r>0.999), the sensitivity was observed to slowly increase or decrease depending upon: 1) the specific metal catalyst immobilized within the hydrogel; and 2) the concentration, exposure time, and nature of the oxidant being examined. For example, when the $Cu^{2+}$/luminol/ Waterlock gel was exposed to a constant concentration of $NO_2(g)$ at 20 ppm, the chemiluminescence signal slowly increased at a rate of approximately 1%/hour. This change in sensitivity is likely attributed to a change in the catalyst or luminol concentration within the gel. The lifetime of these chemiluminescent gels is directly related to the type and concentration of the oxidant, and the extent of exposure. In general, the chemiluminescent gels should be replaced with fresh substrates on a daily basis to maintain accuracy within about 10%.

Figure 8:
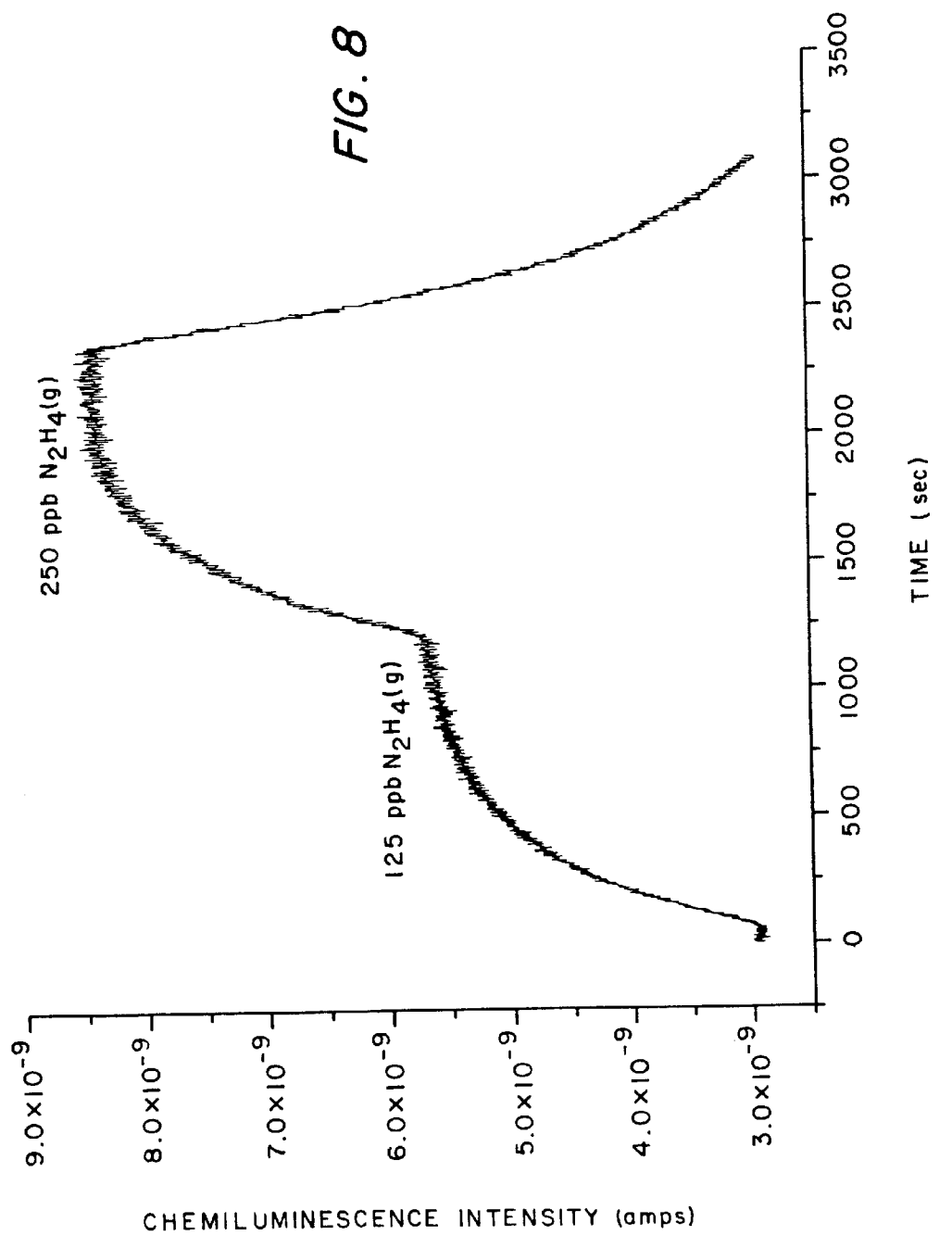
FIG. 8 is an example of the time response obtained for the detection of hydrazine using a Waterlock polymer immobilizing luminol, KOH and colloidal platinum (ascorbic acid reduced).

Tables 3 and 4 also tabulate the sensitivities exhibited by each of the different hydrogels with respect to the detection of several other chemical oxidants and reductants: hydrazine, sulfur dioxide, nitrous oxide and ammonia. Each of the different film compositions were completely unresponsive to NO(g) and $NH_3(g)$. This result can be attributed to the weak, oxidative properties of these molecules with respect to the chemiluminescent oxidation of luminol. Hydrazine and sulfur dioxide, on the other hand, were each detected to varying degrees, although nowhere near the sensitivity shown by nitrogen dioxide. Fortunately with respect to the selective detection of nitrogen dioxide, immobilization of the metal catalyst, Cu(II), resulted in the maximal suppression of any interference due to sulfur dioxide (no response seen for $So_2(g)$ concentrations <3 ppm). Optimal sensitivity for sulfur dioxide was observed using the Waterlock hydrogel to immobilize the metal catalyst, Co(II), and luminol. The detection limit for sulfur dioxide under these film conditions was approximately 37 ppb. The time response for sulfur dioxide is comparable to that seen for nitrogen dioxide, with 90% of full scale observed within one minute. Hydrazine is an extremely strong, reducing agent whose toxic character has generated considerable interest in the development of an effective chemical sensor for this molecule. One would not expect a chemiluminescent reaction to take place between hydrazine and luminol because of the reducing character of hydrazine. Previous investigations with the metal catalyst, colloidal platinum, have suggested that hydrazine is catalytically oxidized at the surface of metal catalysts to form a radical, peroxo intermediate that oxidizes luminol. Collins, et al., *Talanta*, supra. The detection of hydrazine has been demonstrated down to levels as low as 10 ppb in air (signal/ noise=3:1). The response obtained from this sensor for the detection of 125 and 250 ppb hydrazine in dry air is shown in FIG. 8. The detection of $NO_2$ operated on a significantly faster time scale (several seconds) when compared to that obtained while monitoring hydrazine levels (ten minutes). The slow time response evident for the detection of hydrazine is likely attributed to the indirect reaction mechanism involved. In order to be detected, hydrazine vapor must dissolve in the hydrogel film and catalytically react at the surface of a platinum colloid to form a radical peroxo intermediate that can subsequently react with luminol to generate a photon of light. Nitrogen dioxide and oxygen, on the other, react with luminol directly to give a much more rapid chemiluminescent response. The time-domain signal acquired for any particular analyte can be an additional tool for introducing selectivity into these chemical sensors. Kolesar et al., *Proceedings Sensor Expo*, Helmers Publishing, Inc., Peterborough, N.H., 1994; 11–30, for example, has demonstrated the ability to selectively differentiate between $NO_2(g)$ and diisopropyl methylphosphonate (DIMP) using the time- and frequency-domain responses of a copper phthalocyanine-coated IGFET.

Additional Experiments on the Detection of Hydrocarbons

The luminol-based chemiluminescent, chemical sensor described previously was adapted for the detection of volatile, chlorinated organics by adding a pre-oxidative, heated platinum filament to the inlet port leading to the sensor. This pre-stage consists of a platinum wire housed within a small, teflon chamber that contains an inlet and outlet port positioned to direct the gas flow across the length of the filament. The chlorinated hydrocarbons examined in this study were carbon tetrachloride, $CCl_4(g)$, chloroform, $CHCl_3(g)$, and methylene chloride, $CH_2Cl_2(g)$. The filament was held at an estimated temperature of 700° C., a temperature sufficient to achieve partial oxidation or pyrolysis of the chlorinated hydrocarbons prior to their passage across the hydrogel. In fact, over the course of hours of operation with continuous exposure to ppm levels of chlorinated hydrocarbons, the quartz glass window used to separate the hydrogel from the PMT slowly became etched with small pits on the surface of the glass, apparently due to a reaction between the byproducts from the platinum filament and the silicates of the glass. To avoid this problem, a thin, transparent window of teflon was incorporated into the sensor design. Because of the strong chemiluminescence signals evident from the oxidation of luminol by these byproducts, it is believed that the heated platinum filament generates some form of hypochlorite or chlorine radical which has a sufficiently long lifetime to be transported to the sensor surface.

Figure 9:
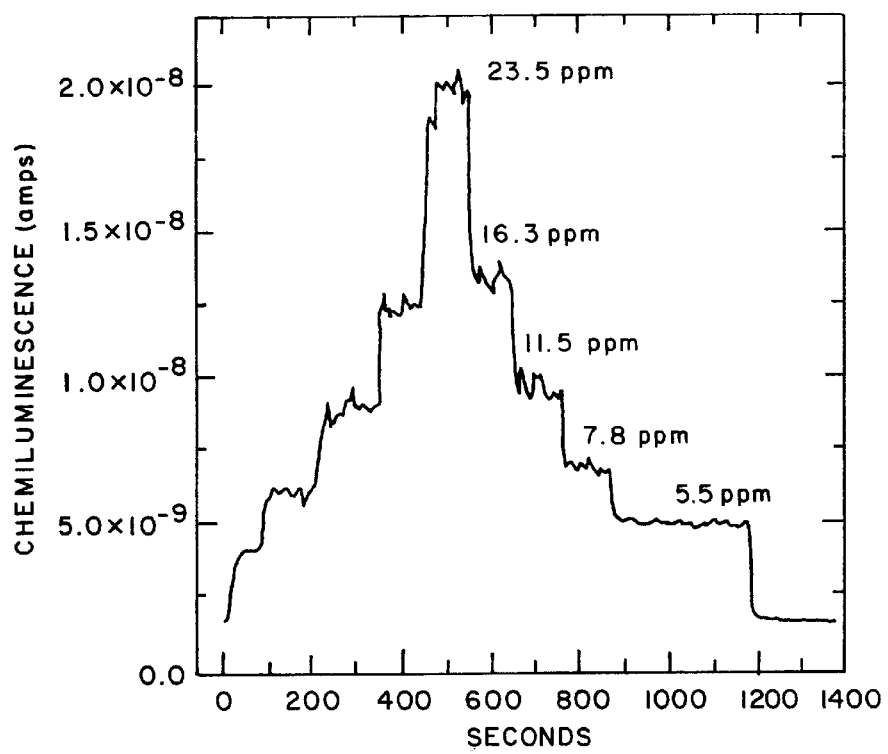
FIG. 9 is a typical response recorded for the detection of chloroform with a Cu(II)/luminol mixture immobilized in the Waterlock hydrogel.

FIG. 9 is a typical response recorded for the detection of chloroform with a Cu(II)/luminol mixture immobilized in the Waterlock hydrogel. This figure demonstrates the ppm detection capabilities of this sensor format for the volatile, chlorinated hydrocarbons. The calculated detection limits for carbon tetrachloride, chloroform, and methylene chloride were 1, 2, and 4 ppm, respectively, based upon a signal/noise ratio of 3:1. The advantage of this system is that the filament can be easily turned on or off, depending upon the sensing needs of the user. The sensitivity exhibited by this sensor is ultimately limited by 1) the efficiency for pyrolysis of the chlorinated hydrocarbons present within the sampled stream of air, 2) the successful transport of the filament byproducts down the inlet line to the sensor surface, and 3) the background chemiluminescence resulting from the oxidation of luminol by oxygen or nitrogen dioxide levels apparent in the sampled air. The linearity of response was reasonable (r>0.99) over the region sampled, although the sensitivity was found to gradually drift with time following continued exposure to ppm levels of analyte (1%/hour). This feature was also noted in the detection of oxygen and nitrogen dioxide, and has been attributed to the oxidation of luminol and/or the gradual elimination of the catalyst.

Figure 10:
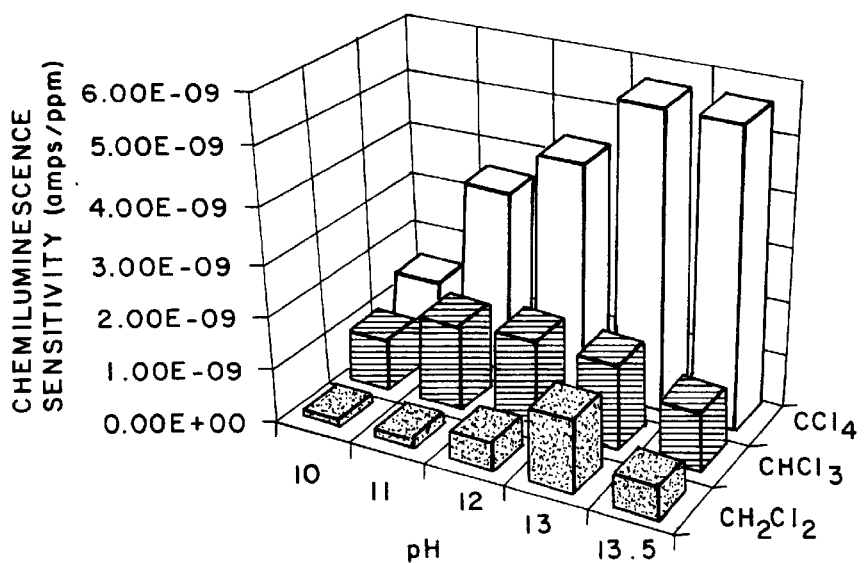
FIG. 10 is a three dimensional plot of the change in sensitivity for a series of Cu(II)/luminol/Waterlock films, each prepared at different buffer pH values, and exposed to $CCl_4(g)$, $CHCl_3(g)$, and $CH_2Cl_2(g)$.

As expected, the buffer pH of the hydrogel strongly dictates the magnitude of the chemiluminescence intensity recorded. FIG. 10 is a three dimensional plot of the change in sensitivity for a series of Cu(II)/luminol/Waterlock films, each prepared at different buffer pH values, and exposed to the three different chlorinated hydrocarbons. The buffer pH could not be examined above pH 13.5, because of the inability of the solution to gel under such alkaline conditions. In general, the sensitivity peaked at a pH of 13, with the sensitivity increasing in the order $CH_2Cl_2(g) < CHCl_3(g) < CCl_4(g)$. This latter trend can be attributed to the increase in the number of available chorine atoms associated with each molecule, and, hence, an increase in the number of oxidative elements present in the gas stream for any given concentration. We may also note from this figure that the signal intensity does not fall off significantly at pH values below 12. Hydrogels prepared at pH 11.5, therefore, will operate with little loss in sensitivity for the chlorinated hydrocarbons, while reporting a significant reduction (>10 times) in interference effects due to $NO_2(g)$. An alternate method for preventing $NO_2(g)$ interference in these chemical sensors which is currently under investigation, is the insertion of a small column of packed Purafil (Doraville, Ga.) into the inlet line prior to the placement of the heated platinum filament. Purafil actively adsorbs all of the $NO_2(g)$ in the carrier stream, while passing the volatile, chlorinated hydrocarbons with reasonable efficiency.

Obviously, many modifications and variations of the present invention are possible in light of the above teachings. It is therefore to be understood that, within the scope of the appended claims, the invention may be practiced otherwise than as specifically described.

What is claimed is:

1. A method for the selective chemiluminescence detection of a vapor-phase analyte in a gas phase including a mixture of gases, comprising the steps of:

exposing a sensing film to said gas phase including said analyte, said sensing film comprising a polymeric film having immobilized therein a chemiluminescent reagent, an optional inorganic catalyst for catalyzing the chemiluminescence interaction between said analyte and said chemiluminescent reagent, and optionally, a buffer, said polymeric film being selectively sorbent for said analyte as a result of solubility interactions between said polymeric film and said analyte, said chemiluminescent reagent having a greater chemiluminescent responsiveness to said analyte than to other components of said gas phase; and detecting any chemiluminescence generated upon said exposure of said sensing film to said, whereby said selective sorption by said polymeric film significantly concentrates said analyte within said film and thus results in a detectable signal greater than that which would occur without said selective sorption.

2. The method of claim 1, wherein said polymeric film is a hydrogel.

3. The method of claim 1, wherein said sensing film includes a catalytically effective concentration of said optional catalyst and said optional catalyst significantly enhances the specificity of said chemiluminescent detection.

4. The method of claim 3, wherein said catalyst is a metal or a metal ion.

5. The method of claim 1, wherein said sensing film includes said buffer in an amount effective to buffer said sensing film.

6. The method of claim 1, wherein said optional catalyst if present, and said optional buffer if present, have a greater chemiluminescent responsiveness to said analyte than to other substances in said gaseous mixture.

7. The method of claim 1, further comprising the step of passing a sample of gas past a heated catalytic metal filament to form said gaseous mixture.

8. The method of claim 1, wherein said analyte is selected from the group consisting of $O_2$, $N_2H_4$, $SO_2$, $NO_2$, and halogenated hydrocarbons.

9. The method of claim 8, wherein said analyte is a halogenated hydrocarbon selected from the group consisting of $CHCl_3$, $CCl_4$, and $CH_2Cl_2$.

10. The method of claim 8, wherein said analyte is $NO_2$.

11. The method of claim 8, wherein said analyte is $O_2$.

12. The method of claim 1, wherein said chemiluminescent reagent is selected from the group consisting of 3-aminophthalhydrazide, dimethylbisacridinium nitrate, siloxene, 2,4,5-triphenylimidazole, bis(2,4,6-trichlorophenyl)oxalate, perylene, and tris(2,2'-bipyridyl)ruthenium(III).

13. The method of claim 12, wherein said chemiluminescent reagent is 3-aminophthalhydrazide.

14. The method of claim 12, wherein said chemiluminescent reagent is tris(2,2'-bipyridyl)ruthenium(III).

15. The method of claim 14, wherein said analyte is $N_2H_4$, $HCH_3N_2H_2$, or $(CH_3)_2N_2H_2$.

16. An apparatus for the selective chemiluminescence detection of a vapor-phase analyte in a gaseous mixture, comprising:

a sensing film, said sensing film having at least one surface exposed to said gaseous mixture, said sensing film comprising a polymeric film having immobilized therein a chemiluminescent reagent, an optional catalyst for catalyzing the chemiluminescent interaction between said analyte and said chemiluminescent reagent, and optionally, a buffer, said polymeric film being selectively sorbent for said analyte, said chemiluminescent reagent having a greater chemiluminescent responsiveness to said analyte than to other components of said gaseous mixture; and a detecting means for detecting any chemiluminescence generated upon said exposure of said sensing film to said gaseous mixture.

17. The apparatus of claim 16, wherein said detecting means comprises a photomultiplier tube.

18. The apparatus of claim 16, wherein said detecting means comprises a photodiode.

19. The apparatus of claim 16, wherein said polymeric film is a hydrogel.

20. The method of claim 1, wherein said analyte is a hydrazine or a halogenated hydrocarbon.

21. The method of claim 20, wherein said analyte is $N_2H_4$, $HCH_3N_2H_2$, $(CH_3)_2N_2H_2$, or a halogenated hydrocarbon.

22. The method of claim 21, wherein said halogenated hydrocarbon is $CHCl_3$, $CCl_4$, or $CH_2Cl_2$.

* * * * *